United States Patent [19]
Hsieh

[11] Patent Number: 5,835,559
[45] Date of Patent: Nov. 10, 1998

[54] METHODS AND APPARATUS FOR SCANNING AN OBJECT IN A COMPUTED TOMOGRAPHY SYSTEM

[75] Inventor: Jiang Hsieh, Waukesha, Wis.

[73] Assignee: General Electric Company, Milwaukee, Wis.

[21] Appl. No.: 880,474

[22] Filed: Jun. 23, 1997

[51] Int. Cl.[6] ........................................... A61B 6/03
[52] U.S. Cl. .................. 378/4; 378/62; 378/901
[58] Field of Search .................. 378/4, 11, 14, 378/19, 901, 62, 98, 2

[56] References Cited

U.S. PATENT DOCUMENTS 5,579,359  11/1996  Toth ........................................... 378/19
5,610,963  3/1997  Hsieh .......................................... 378/7

*Primary Examiner*—David P. Porta
*Assistant Examiner*—David Vernon Bruce
*Attorney, Agent, or Firm*—John S. Beulick; John H. Pilarski

[57] ABSTRACT

The present invention, in one form, is a system for generating a high resolution image of an object from projection data acquired during a computed tomography scan. The system includes a gantry having an x-ray source which rotates around the object and emits an x-ray beam toward a detector. The system identifies a region of x-ray beam movement and divides the region into subregions. Linear Q-CAL vectors are then generated for each subregion so that each vector is representative of detector gain in one of the subregions. These Q-CAL vectors are then applied to projection data to generate image data.

18 Claims, 2 Drawing Sheets

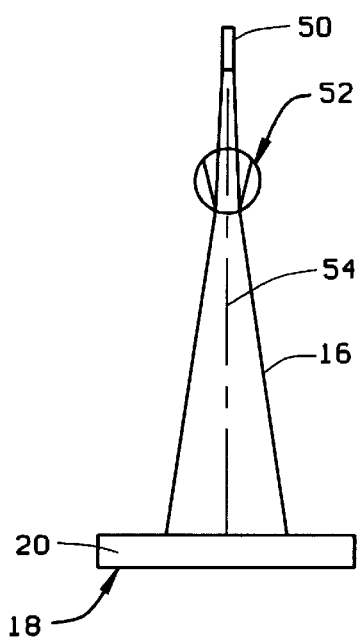
FIG. 3
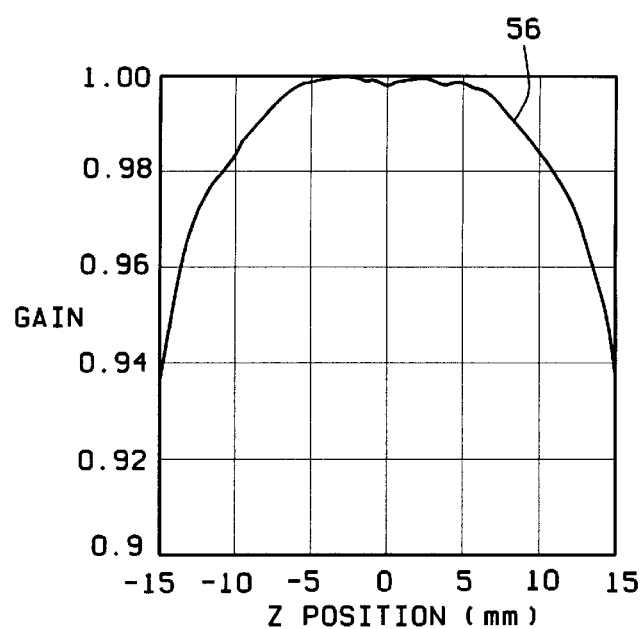
FIG. 4
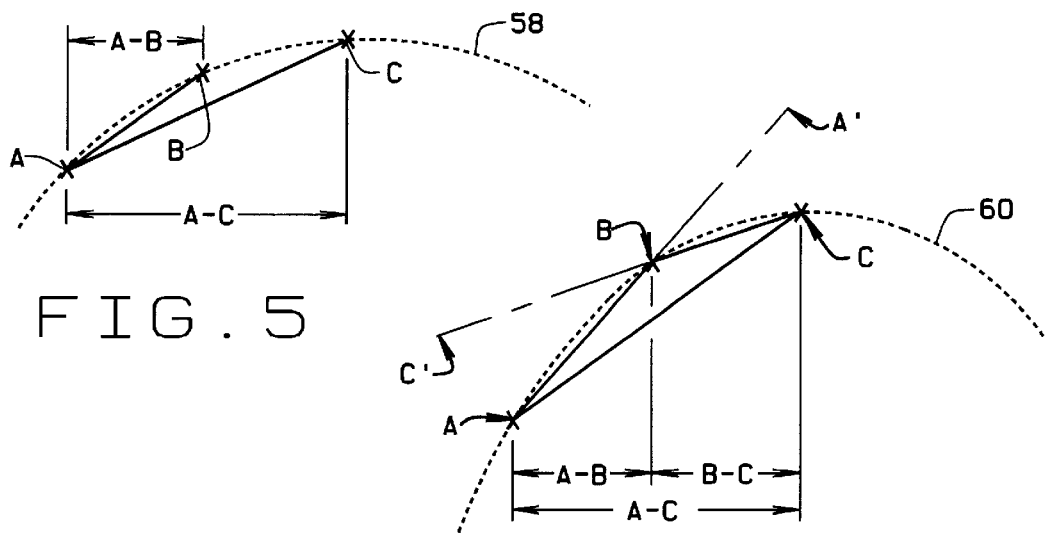
FIG. 5
FIG. 6
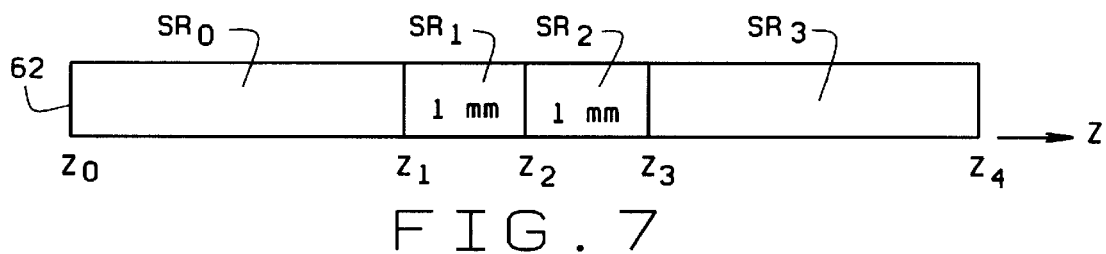
FIG. 7

METHODS AND APPARATUS FOR SCANNING AN OBJECT IN A COMPUTED TOMOGRAPHY SYSTEM

FIELD OF THE INVENTION

This invention relates generally to computed tomography (CT) imaging and, more particularly, to scanning an object of interest with a CT scanner.

BACKGROUND OF THE INVENTION

In at least one known CT system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The detectors are generally rectangular. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles during one revolution of the x-ray source and detector. In an axial scan, the projection data is processed to construct an image that corresponds to a two dimensional slice taken through the object. Typically, the configuration of a slice may be varied. One method for reconstructing an image from a set of projection data is referred to in the art as the filtered back projection technique. This process converts that attenuation measurements from a scan into integers called "CT numbers" or "Hounsfield units", which are used to control the brightness of a corresponding pixel on a cathode ray tube display.

To reduce the total scan time required for multiple slices, a "helical" scan may be performed. To perform a "helical" scan, the patient is moved in the z-axis synchronously with the rotation of the gantry, while the data for the prescribed number of slices is acquired. Such a system generates a single helix from a fan beam helical scan. The helix mapped out by the fan beam yields projection data from which images in each prescribed slice may be reconstructed. In addition to reduced scanning time, helical scanning provides other advantages such as better use of injected contrast, improved image reconstruction at arbitrary locations, and better three-dimensional images.

The x-ray source typically includes an evacuated x-ray envelope containing an anode and a cathode. X-rays are produced when electrons from the cathode are accelerated against a focal spot on the anode by applying a high voltage across the anode and cathode. The x-rays diverge from the focal spot in a generally conical pattern.

In known CT systems, an x-ray may become off-centered during a scan operation, which is undesirable. For example, as the x-ray source heats up, the thermal expansion of the anode may cause the focal spot to move. Also, as the gantry rotates, mechanical stresses on the gantry and x-ray source may cause additional focal spot motion. This focal spot movement translates into x-ray beam movement on the detector along the z direction. Such movement typically causes image artifacts because the detector sensitivity, e.g., the detector gain, varies across the detector in the z-direction.

Many CT systems utilize z-axis calibration vectors, sometimes referred to as Q-CAL vectors, to correct for focal spot movement. These vectors typically are representative of detector gain in the z-direction, and are applied to projection data in accordance with the distance between the x-ray beam and its reference point.

For example, one method of determining Q-CAL vectors requires identifying a region of x-ray beam movement and generating a linear Q-CAL vector using linear approximation. The region of x-ray beam movement is identified by performing gain readings at two locations on the detector. Specifically, the gain readings are taken at the location of the x-ray beam when the x-ray tube is cool and the location of the x-ray beam when the x-ray tube is hot. A linear function is assumed for the detector gains between these two locations, and the Q-CAL vector is generated so that it is representative of the slope of the detector sensitivity between the two locations. During a CT scan, the x-ray beam location is measured and the projection readings, i.e., projection data, are adjusted based on the Q-CAL vector and the distance of the beam from its reference point.

Linear Q-CAL vectors, while generally effective for a small amount of x-ray beam movement, often are not effective for a large amount of x-ray beam movement. Particularly, detector gain typically varies in accordance with a curved function, rather than a linear function, over the detector. Accordingly, over large areas of x-ray beam movement, the linear Q-CAL vector may be substantially different from the curved detector gain function.

To better approximate the curved detector gain function, some CT systems generate second order or higher order Q-CAL vectors. In general, a higher order Q-CAL vector provides a better estimation of the detector z-axis profile. However, the higher order Q-CAL vectors sometimes are unstable, and in some cases even are inferior to linear Q-CAL vectors.

It would be desirable to substantially reduce artifacts caused by focal spot movement over both a small area and a large area of the detector. It also would be desirable to provide such improved image quality without requiring significant hardware and software changes in known CT systems.

SUMMARY OF THE INVENTION

These and other objects may be attained in a CT system which, in one embodiment, implements a piece-wise Q-CAL correction algorithm. Particularly, a region of x-ray beam motion is identified and divided into subregions. Linear Q-CAL vectors are then generated for each subregion so that each vector is representative of detector gain in one of the subregions. These Q-CAL vectors are then applied to projection data to generate image data.

It is believed that the above described Q-CAL correction algorithm reduces artifacts typically caused by focal spot movement over both large and small regions. It also believed that such algorithm is more stable than utilizing second order or higher order Q-CAL vectors. In addition, it is believed that such algorithm provides improved image quality without requiring significant hardware and software changes in known CT systems.

BRIEF DESCRIPTION OF THE DRAWINGS

FIG. 3 is a schematic view of a CT imaging system with a collimator.

FIG. 4 is a graphical illustration of a typical detector sensitivity profile.

FIG. 5 is a graphic illustration of known linear Q-CAL estimation applied over two different regions of x-ray beam movement.

FIG. 6 is a graphic illustration of piece-wise Q-CAL estimation over a large x-ray beam movement in accordance with one embodiment of the present invention.

FIG. 7 is a pictorial view of a region of x-ray beam movement divided into subregions in accordance with one embodiment of the present invention.

DETAILED DESCRIPTION

Figure 1:
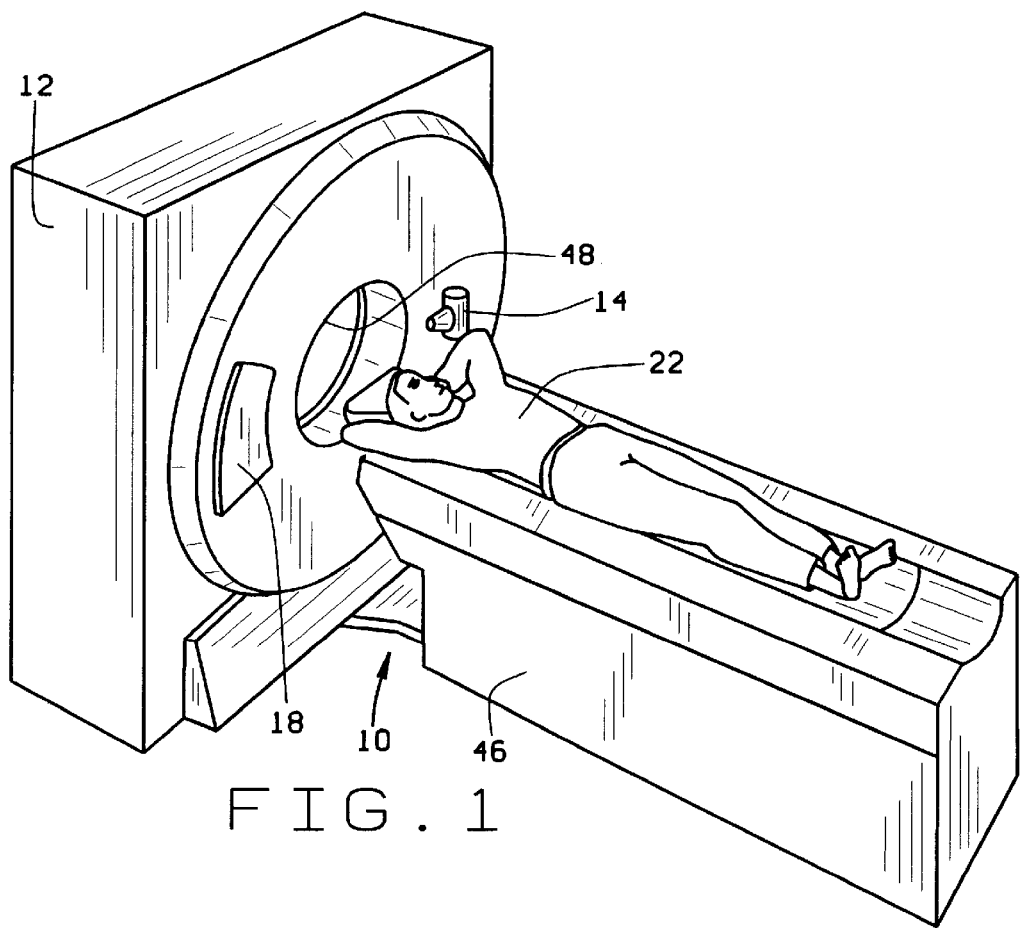
FIG. 1 is a pictorial view of a CT imaging system.
Figure 2:
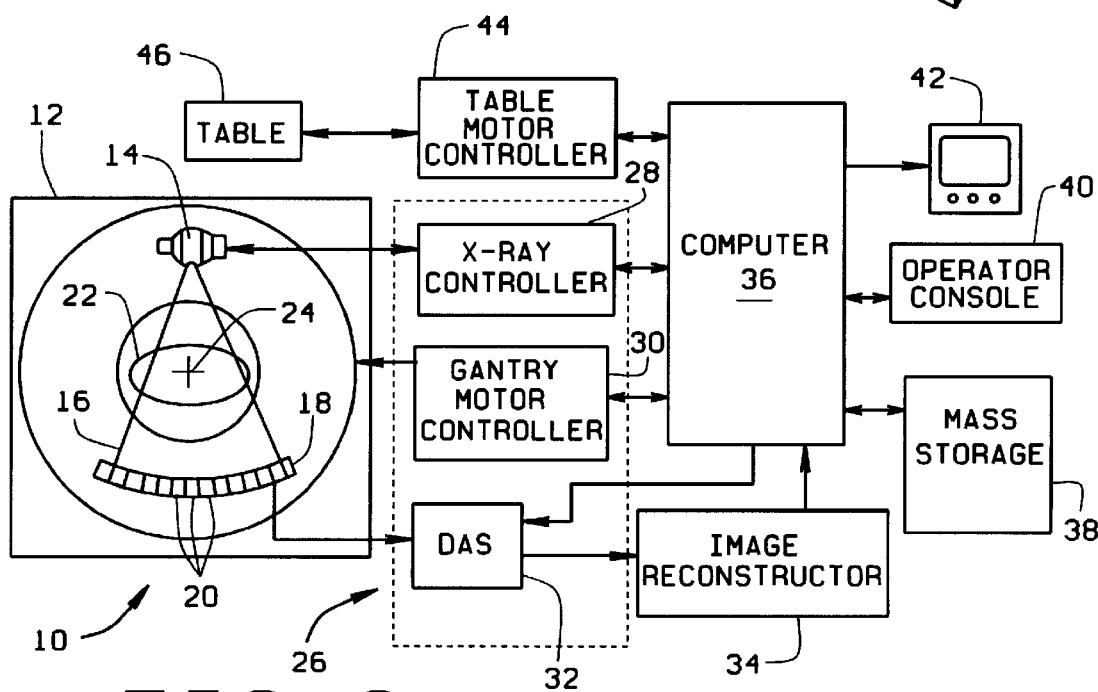
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a fan beam of x-rays 16 toward a detector array 18 on the opposite side of gantry 12. Detector array 18 is formed by detector elements 20 which together sense the projected x-rays that pass through a medical patient 22. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Referring to FIG. 3, and with respect to operation of x-ray source 14, x-ray beam 16 emanates from a focal spot 50 of source 14. Particularly, x-ray beam 16 emanates from focal spot 50 of an anode, or x-ray tube. X-ray beam 16 is collimated by collimator 52, and collimated beam 16 is projected toward detector array 18 along a fan beam axis 54 centered within fan beam 16.

As explained above, an x-ray may become off-centered during a scan operation, which is undesirable. For example, as the x-ray source heats up, the thermal expansion of the anode may cause the focal spot to move. Also, as the gantry rotates, mechanical stresses on the gantry and x-ray source may cause additional focal spot motion. This focal spot movement translates into an x-ray beam movement on the detector along the z direction.

FIG. 4 is a graphical illustration of a typical detector sensitivity profile 56, i.e., detector cell gain versus x-ray beam location on detector 18. As clearly shown, detector sensitivity profile 56 is not uniform along the z direction. Particularly, the detector gain is a function of the location of x-ray beam 16 on detector 18. Failure to correct projection data in accordance with detector profile 56 typically causes image artifacts.

Known CT systems, as explained above, utilize a linear Q-CAL correction scheme to overcome the detector z-axis profile non-uniformity. The correction scheme typically requires performing gain readings at two locations on detector 18 before scanning an object. Typically, the locations are the location of x-ray beam 16 on detector 18 when the x-ray tube is cool and the location of x-ray beam 16 on detector 18 when the x-ray tube is hot. A linear function then is assumed about the detector gain between these two locations, and a Q-CAL vector is generated so that it is representative of the slope of the detector sensitivity between the two locations. During a CT scan of the object, the location of x-ray beam 16 on detector 18 is measured and the projection readings, i.e., projection data, are adjusted based on the Q-CAL vector and the distance of beam 16 from its reference point.

FIG. 5 is a graphic illustration of known linear Q-CAL estimation applied over two different regions of x-ray beam movement on a detector having a sensitivity profile 58. With respect to a small region x-ray beam movement A-B, a first gain reading is performed at a first location A and a second gain reading is performed at a second location B on the detector. Assuming a linear function between locations A and B, a Q-CAL vector is generated so that it is representative of the slope of detector sensitivity 58 between locations A and B, i.e., the line AB. The Q-CAL vector generated for small region of movement A-B closely approximates detector sensitivity profile 58 between location A and location B, and is generally acceptable for other small regions of x-ray beam movement.

Known linear Q-CAL estimation, however, often is not acceptable for large regions x-ray beam movement. For example, and with respect to a large region of x-ray beam movement A-C, first gain reading is performed at first location A and a second gain reading is performed at a second location C on the detector. Assuming a linear function between locations A and C, a Q-CAL vector is generated so that it is representative of the slope of detector sensitivity 58 between locations A and C, i.e., the line AC. The Q-CAL vector generated for large region of movement A-C, as shown, does not closely approximate detector sensitivity profile 58 between location A and location C. Until now, it was believed that to better approximate detector sensitivity profile 58 over a large region x-ray beam movement, e.g., region A-C, a second or even higher order Q-CAL estimation algorithm was required. However, and as explained above, such higher order estimation algorithms often are unstable, and thus may, at times, be inferior to linear Q-CAL estimation algorithms.

In accordance with one embodiment of the present invention, a piece-wise Q-CAL correction algorithm is utilized to approximate detector sensitivity profile over both a small region and a large region of x-ray beam movement. The present correction algorithm is not directed to, nor limited to practice with, any particularly image reconstruction algorithm. Rather, the present correction algorithm may be used in conjunction with many different helical reconstruction algorithms and axial reconstruction algorithms. Also, although the present correction algorithm is sometimes described herein in connection with a third generation CT system, the present algorithm can be practiced in connection with may other types of CT system, including fourth generation CT systems. Further, in one embodiment, the correction algorithm would be implemented in computer 36 and would process, for example, data stored in mass storage 38. Many other alternative implementations are, of course, possible.

In accordance with one embodiment of the present invention, a region of x-ray beam motion is identified and divided into subregions. Linear Q-CAL vectors are then generated for each subregion so that each vector is representative of detector gain in one of the subregions. Particularly, instead of treating an entire region of x-ray beam motion as a single entity, such region is divided into subregions, and linear Q-CAL correction is performed subregion.

FIG. 6 is a graphic illustration of piece-wise Q-CAL estimation applied over a large region of x-ray beam movement A-C on a detector having a sensitivity profile 60 in accordance with one embodiment of the present invention. A first gain reading is performed at a first location A, e.g., the location of x-ray beam 16 on detector 18 when the x-ray tube is cool. A second gain reading is performed at a second location C, e.g., the location of x-ray beam 16 on detector 18 when the x-ray tube is hot. The region A-C substantially defines the region of x-ray beam motion.

Region A-C is divided into two subregions by performing a third gain reading at a third location B, which is between first location A and third location C. Accordingly, region A-C is divided into a first subregion A-B and a second subregion B-C. Of course, region A-C may be divided into more than two, e.g., three, four, or even more, subregions.

Within each subregion A-B and B-C, linear Q-CAL estimation is performed to generate a Q-CAL vector which substantially approximates the sensitivity profile within such region A-B and B-C, respectively. For example, and for first subregion A-B, a linear function is assumed between locations A and B, and a first linear Q-CAL vector is generated which is representative of the slope of the detector sensitivity between locations A and B. The first Q-CAL vector, i.e., the line AB, closely approximates detector sensitivity profile 60 between location A and location B. Similarly, and for subregion B-C, a linear function is assumed between locations B and C, and a second linear Q-CAL vector is generated which is representative of the slope of the detector sensitivity between locations B and C. The second Q-CAL vector, i.e., the line BC, closely approximates the detector sensitivity profile (dashed line) between location B and location C.

During a CT scan, the first and second Q-CAL vectors are applied to projection data obtained at the detector, in accordance with the location of the x-ray beam, to generate an image. For example, the first Q-CAL vector is applied to projection data obtained when the x-ray beam is located in subregion A-B and the second Q-CAL vector is applied to projection data obtained when the x-ray beam is located in subregion B-C.

Continuity between subregion A-B and subregion B-C is substantially ensured because third location B is used as reference point for both subregions A-B and B-C. In addition, and because linear Q-CAL correction is performed in each subregion A-B and B-C, the piece-wise Q-CAL correction algorithm is not believed to suffer from any stability problem, such as often suffered by second order or higher order Q-CAL algorithms.

Interpolative Piece-wise Q-CAL Correction (IPQ) algorithms may be used to even better approximate detector sensitivity profile 60 across x-ray beam region of movement A-C. Particularly, a correction term may be added to the linear Q-CAL estimation in each subregion A-B and B-C to better approximate detector sensitivity within subregions A-B and B-C, respectively. With respect to first subregion A-B, detector sensitivity profile 60 for first subregion A-B is between the linear Q-CAL estimate for subregion A-B, e.g., the line AB, and an extension of the linear Q-CAL estimation from adjacent subregion B-C, e.g., a line between B and C'. The correction term is determined utilizing the extension of the linear Q-CAL estimation from adjacent subregion B-C, which is merely a linear extension of the line BC, and added to the piece-wise Q-CAL estimation for subregion A-B.

Similarly, and with respect to second subregion B-C, detector sensitivity profile 60 for second subregion B-C is between the linear Q-CAL estimate for subregion B-C, e.g., the line BC, and an extension of the linear Q-CAL estimation from adjacent subregion A-B, e.g., a line between B and A'. The correction term, accordingly, is determined utilizing the extension of the linear Q-CAL estimation from adjacent subregion A-B, which is merely a linear extension of the line AB, and added to the piece-wise Q-CAL estimation for second subregion B-C.

The correction term is selected to satisfy the following conditions: at locations A, B and C, the correction term is substantially zero; and the correction term is substantially continuous in region of movement A-C. Such conditions substantially ensure that the estimation equals true detector profile 60 at each location A and B and C. The correction term may be stored, for example, in mass storage 38 or a memory of computer 36.

As one specific example, FIG. 7 is a pictorial view of a detector 62 divided along a z-axis into four subregions $SR_0$, $SR_1$, $SR_2$ and $SR_3$. Subregion $SR_0$ extends between a location $z_0$ and a location $z_1$, subregion $SR_1$ extends between location $z_1$ and a location $z_2$, subregion $SR_2$ extends between location $z_2$ and a location $z_3$, and subregion $SR_3$ extends between location $z_3$ and a location $z_4$. Location $z_2$ is substantially centered within detector 62, and subregions $SR_1$ and $SR_2$ each cover approximately 1 mm of the central portion of detector 62, and thus approximately 2 mm of x-ray beam movement along detector 62. If $Q_1(z)$ denotes a piece-wise Q-CAL estimation of the detector profile at a location z based on subregion $SR_1$, e.g., line A–A' (FIG. 6), and $Q_2(z)$ denotes the piece-wise Q-CAL estimation of the detector profile at location z based on subregion $SR_2$, e.g., line C–C' (FIG. 6), an IPQ can be expressed by the equation:

$$Q(z) = \begin{cases} Q_1(z) & z_0 \leq z < z_1 \\ Q_1(z) + \beta\Delta_1 \left[ 1 - \dfrac{2|z - z_{m1}|}{(z_2 - z_1)} \right] & z_1 \leq z < z_2 \\ Q_2(z) + \beta\Delta_2 \left[ 1 - \dfrac{2|z - z_{m2}|}{(z_3 - z_2)} \right] & z_2 \leq z < z_3 \\ Q_2(z) & z_3 \leq z < z_4 \end{cases}$$

where:

$z_{mX}$ represents a center of subregion $SR_X$;

$\beta$ is a scaling constant;

$\Delta_1 = Q_2(z_{m1}) - Q_1(z_{m1})$; and $\Delta_2 = Q_1(z_{m2}) - Q_2(z_{m2})$.

In accordance with one embodiment, scaling constant $\beta=0.3$. Of course, scaling constant $\beta$ may have values other than 0.3. Accordingly, correction terms are added to the piece-wise Q-CAL estimation for subregions $SR_1$ and $SR_2$, while correction terms are not added to the piece-wise Q-CAL estimation for subregions $SR_0$ and $SR_3$. Of course, many different equations, or IPQ algorithms, can satisfy the conditions identified above, and correction terms may be added to either fewer of more of subregions $SR_0$, $SR_1$, $SR_2$ and $SR_3$.

It is believed that the above described piece-wise Q-CAL correction algorithm and IPQ algorithm reduce artifacts typically caused by focal spot movement over both large and small regions. It also believed that such algorithms are more stable than utilizing second order or higher order Q-CAL vectors. In addition, it is believed that such algorithms provide improved image quality without requiring significant hardware and software changes in known CT systems.

It further is believed that such algorithms facilitate improving image quality even where the gantry includes deteriorated detectors. Particularly, deteriorated detectors typically exhibit much larger sensitivity variations in the z direction than non-deteriorated detectors, which typically reduces the effectiveness of known Q-CAL. However, the piece-wise correction algorithm and IPQ algorithm described above are believed to substantially overcome such sensitivity.

From the preceding description of various embodiments of the present invention, it is evident that the objects of the invention are attained. Although the invention has been described and illustrated in detail, it is to be clearly understood that the same is intended by way of illustration and example only and is not to be taken by way of limitation. For example, the CT system described herein is a "third generation" system in which both the x-ray source and detector rotate with the gantry. Many other CT systems including multislice systems, electron beam systems, and "fourth generation" systems wherein the detector is a full-ring stationary detector and only the x-ray source rotates with the gantry, may be used. Furthermore, while the correction algorithms were described in connection with substantially concave detector sensitivity profiles, such algorithms may also be implemented with other detector sensitivity profiles including substantially convex detector sensitivity profiles. Accordingly, the spirit and scope of the invention are to be limited only by the terms of the appended claims.

I claim:

1. A method for generating image data of an object scanned by a computed tomography system, the computed tomography system including a gantry having an x-ray source for projecting an x-ray beam toward a detector, the x-ray source including an x-ray tube, said method comprising the steps of:

identifying a region of x-ray beam movement;

dividing the region into at least two subregions;

generating a Q-CAL vector for at least one of the subregions.

2. A method in accordance with claim 1 wherein generating a Q-CAL vector for at least one of the subregions comprises the step of generating a linear Q-CAL vector.

3. A method in accordance with claim 1 comprising the step of dividing the region into two subregions.

4. A method in accordance with claim 1 comprising the step of generating a Q-CAL vector for each subregion.

5. A method in accordance with claim 1 further comprising the step of adding a correction term to at least one of the Q-CAL vectors.

6. A method in accordance with claim 1 wherein dividing the region into at least two subregions comprises the step of dividing the region into four subregions.

7. A method in accordance with claim 6 wherein the Q-CAL vectors are generated in accordance with:

$$Q(z) = \begin{cases} Q_1(z) & z_0 \leq z < z_1 \\ Q_1(z) + \beta\Delta_1 \left[ 1 - \dfrac{2|z - z_{m1}|}{(z_2 - z_1)} \right] & z_1 \leq z < z_2 \\ Q_2(z) + \beta\Delta_2 \left[ 1 - \dfrac{2|z - z_{m2}|}{(z_3 - z_2)} \right] & z_2 \leq z < z_3 \\ Q_2(z) & z_3 \leq z < z_4 \end{cases}$$

where:

$z_{mX}$ represents a center of subregion $SR_X$;

$\beta$ is a scaling constant;

$\Delta_1 = Q_2(z_{m1}) - Q_1(z_{m1})$; and $\Delta_2 = Q_1(z_{m2}) - Q_2(z_{m2})$.

8. A method in accordance with claim 1 wherein identifying a region of x-ray beam movement comprises the steps of:

performing a first gain reading at a first location; and performing a second gain reading at a second location.

9. A method in accordance with claim 8 wherein said first gain reading is performed when the x-ray tube is cool and wherein said second gain reading is performed when the x-ray tube is hot.

10. A system for generating image data of an object, said system comprising a gantry having an x-ray source for projecting an x-ray beam toward a detector, said system configured to:

identify a region of x-ray beam movement;

divide the region into at least two subregions;

generate a Q-CAL vector for at least one of the subregions.

11. A system in accordance with claim 10 configured to generate a linear Q-CAL vector for at least one of the subregions.

12. A system in accordance with claim 10 configured to dividing the region into two subregions.

13. A system in accordance with claim 10 configured to generate a Q-CAL vector for each subregion.

14. A system in accordance with claim 10 further configured to add a correction term to at least one of the Q-CAL vectors.

15. A system in accordance with claim 10 configured to divide the region into four subregions.

16. A system in accordance with claim 15 configured to generate a Q-CAL vector in accordance with:

$$Q(z) = \begin{cases} Q_1(z) & z_0 \leq z < z_1 \\ Q_1(z) + \beta\Delta_1 \left[ 1 - \frac{2|z - z_{m1}|}{(z_2 - z_1)} \right] & z_1 \leq z < z_2 \\ Q_2(z) + \beta\Delta_2 \left[ 1 - \frac{2|z - z_{m2}|}{(z_3 - z_2)} \right] & z_2 \leq z < z_3 \\ Q_2(z) & z_3 \leq z < z_4 \end{cases}$$

where:

$Z_{mx}$ represents a center of subregion $SR_x$;

$\beta$ is a scaling constant;

$\Delta_1 = Q_2(z_{m1}) - Q_1(z_{m1})$; and $\Delta_2 = Q_1(z_{m2}) - Q_2(z_{m2})$.

17. A system in accordance with claim 10 wherein to identify the region of x-ray beam movement, said system is configured to:

perform a first gain reading at a first location; and perform a second gain reading at a second location.

18. A system in accordance with claim 17 wherein said first gain reading is performed when the x-ray tube is cool and wherein said second gain reading is performed when the x-ray tube is hot.

\* \* \* \* \*